(12) United States Patent
Krzysik et al.

(10) Patent No.: US 7,666,824 B2
(45) Date of Patent: Feb. 23, 2010

(54) LIQUID CLEANSER COMPOSITIONS

(75) Inventors: Duane G. Krzysik, Appleton, WI (US); Julie M. Utschig, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 684 days.

(21) Appl. No.: 10/829,518

(22) Filed: Apr. 22, 2004

(65) Prior Publication Data

US 2005/0239669 A1 Oct. 27, 2005

(51) Int. Cl.
*A61K 7/50* (2006.01)

(52) U.S. Cl. .................. 510/130; 510/119; 510/124; 510/156; 510/424; 510/428

(58) Field of Classification Search .................. None
See application file for complete search history.

(56) References Cited

U.S. PATENT DOCUMENTS

| | | | |
|---|---|---|---|
| 3,829,563 A * | 8/1974 | Barry et al. | .................. 510/124 |
| 5,952,285 A | 9/1999 | Hawkins | |
| 5,952,286 A | 9/1999 | Puvvada et al. | |
| 6,090,762 A | 7/2000 | Clapperton et al. | |
| 6,126,954 A | 10/2000 | Tsaur | |
| 6,150,312 A | 11/2000 | Puvvada et al. | |
| 6,177,396 B1 | 1/2001 | Clapperton et al. | |
| 6,395,690 B1 | 5/2002 | Tsaur | |
| 6,395,691 B1 | 5/2002 | Tsaur | |

FOREIGN PATENT DOCUMENTS

| | | |
|---|---|---|
| EP | 0 419 164 A1 | 3/1991 |
| WO | WO 01/19949 A1 | 3/2001 |

OTHER PUBLICATIONS

International Search Report from PCT/US2005/003607 dated Jul. 5, 2005.

* cited by examiner

*Primary Examiner*—Necholus Ogden, Jr.
(74) *Attorney, Agent, or Firm*—Armstrong Teasdale LLP

(57) ABSTRACT

Aqueous liquid cleanser compositions are disclosed. The cleanser compositions are structured liquids capable of suspending a skin benefit agent therein to improve transfer of the skin benefit agent to the skin upon use of the wash. In one embodiment, the skin benefit agent is a lipid material, which remains on the skin after washing to provide skin barrier enhancement.

54 Claims, No Drawings

LIQUID CLEANSER COMPOSITIONS

BACKGROUND OF THE INVENTION

The present invention is directed to stable structured liquid cleanser compositions. More particularly, the present invention is directed to structured liquid cleansing compositions such as a facial wash, body wash, or baby wash. Along with cleansing, the structured liquid cleanser compositions introduce onto the skin a beneficial component such as a skin barrier enhancing agent or a skin protectant. The compositions are capable of suspending the beneficial component in the composition such that transfer to the skin of the beneficial component is improved over conventional surfactant-based cleansing products.

The stratum corneum is the outer-most layer of the skin and is responsible for regulating skin water levels and functioning as a barrier against chemicals and other stressors found in the environment. The complex arrangement of lipids in the intercellular space of the stratum corneum is responsible for the establishment of normal barrier function. Multi-layered structures of cholesterol, ceramides, and fatty acids, as well as some other minor lipids, provides the major barrier to the transport of hydrophilic substances into or through the skin.

In order to protect and care for the stratum corneum, and skin in general, most people frequently clean skin to remove dirt, contaminants, and bacteria. Many different types of skin cleansing formulations are commercially available, including, for example, hand washes, face washes, and body washes. Along with surfactants for cleaning, many of the commercially available washes additionally include one or more skin benefit agents for application to the skin during washing. These agents may include, for example, moisturizers, lipids, oils, and the like.

In many cases, in order for the skin benefit agent to be easily transferable to the skin and/or deposited thereon from the wash formulation, the skin benefit agent must be emulsified in the wash product to keep it from settling to the bottom of the product. Although this does allow for the benefit ingredient to be suspended in the wash formulation, once emulsified, a majority of the benefit agent may simply be washed away and not contact, or be deposited on, the surface of the skin. Additionally, even if the benefit ingredient does contact the skin, it may be washed away during the rinsing of the wash product from the skin.

Based on the foregoing, it would be beneficial to provide skin wash products that include a skin benefit ingredient, such as a barrier enhancing agent, for example, that can be easily transferred to the skin from the wash product. Additionally, it would be beneficial if the skin benefit ingredient remained on the skin after washing such that the benefit could be improved.

SUMMARY OF THE INVENTION

The present invention is directed to stable structured liquid cleansing compositions comprising small droplets or particulates of skin benefit ingredients. Stability of the composition and suspension of the skin benefit ingredient is achieved by the structure and to a certain extent the viscosity produced by surfactants present in the composition, which are in a lamellar phase. Because the skin benefit ingredient is included in the structured liquid composition in droplet form less than about 30 micrometers and is suspended rather than emulsified, the benefit ingredient is easily transferred to the skin and substantially remains on the skin after washing to achieve the desired benefit.

Therefore, the present invention is directed to a liquid cleanser composition comprising a lamellar structured liquid. The liquid comprises from about 30% (by weight) to about 80% (by weight) of a surfactant, from about 1% (by weight) to about 30% (by weight) of a lipid phase, and from about 19% (by weight) to about 69% (by weight) water. The lipid phase comprises from about 1% (by weight) to about 5% (by weight) of a sterol and from about 95% (by weight) to about 99% (by weight) of a natural fat or oil. The liquid cleanser composition has a viscosity of from about 10,000 cps to about 300,000 cps.

The present invention is further directed to a liquid cleanser composition comprising a lamellar structured liquid. The liquid comprises from about 30% (by weight) to about 80% (by weight) of a surfactant, from about 1% (by weight) to about 30% (by weight) of a skin protectant, and from about 19% (by weight) to about 69% (by weight) water. The liquid cleanser composition has a viscosity of from about 10,000 cps to about 300,000 cps.

The present invention is further directed to a liquid cleanser composition comprising a lamellar structured liquid. The liquid comprises from about 30% (by weight) to about 80% (by weight) of a surfactant, from about 1% (by weight) to about 30% (by weight) of a sunscreen active, and from about 19% (by weight) to about 69% (by weight) water. The liquid cleanser composition has a viscosity of from about 10,000 cps to about 300,000 cps.

DETAILED DESCRIPTION OF THE PRESENTLY PREFERRED EMBODIMENTS

The present invention is generally directed to stable structured liquid cleansing compositions that provide a skin benefit upon application and use. The compositions are formulated in such a manner that the cleansing surfactants present in the composition form a lamellar phase that enables the suspension of one or more skin benefit ingredients therein. Because the skin benefit ingredient, which may be a lipid for example, is not emulsified into the composition, the ingredient is more easily deposited on the skin during the washing process. Additionally, because the skin benefit ingredient is formulated such that it is present in small droplets, a substantial amount of the ingredient remains on the skin after washing and rinsing to provide the intended benefit.

The liquid cleanser compositions described herein may be formulated as a number of different types of washes for ultimate sale to a consumer. For example, the compositions may comprise facial washes, body washes, hand washes, baby washes, and the like. Additionally, the compositions may comprise shampoos or other hair and scalp-treating products.

As noted above, the aqueous liquid cleanser compositions described herein comprise from about 19% (by weight) to about 69% (by weight) water. As used herein, the term "by weight" refers to the total weight of the liquid cleanser composition, including all components thereof. For example, if the liquid cleanser composition comprised 19% (by weight) water, and had a total weight of 100 grams, the liquid cleanser composition would comprise 19 grams of water.

The liquid cleanser composition additionally comprises from about 30% (by weight) to about 80% (by weight) of a surfactant. The surfactant component or system is included in the liquid cleanser composition to provide a cleaning, lathering, and/or foaming action during the use of the product, along with a structured liquid system. Although commonly referred to herein in the singular, it should be recognized that the liquid cleanser compositions described herein may comprise a single surfactant, or may comprise a combination of two, three, four, or more surfactants to obtain the desired properties of the product. As noted above, the suspension of various skin benefit ingredients, which can be oil droplets or particulates, for example, is a function of both the structure of the composition and its viscosity.

The liquid cleanser compositions are formulated in such a manner that the surfactant present forms a lamellar phase in solution; that is, the surfactant forms lamellar-like sheets in the solution that form together like layers of an onion that prevent the skin benefit ingredient from rising to the surface or falling to the bottom of the composition. These lamellar structured liquids are concentrated surfactant systems that allow for the suspension therein of droplets of oils, particulates, or other components. Because these structured systems allow for long term suspension of a desired skin benefit ingredient, emulsification of the skin benefit ingredient into the liquid is not required to keep the skin benefit ingredient from settling out. This is advantageous as the skin benefit ingredient can then be more easily transferred to the skin during use of the product as the emulsion does not have to be broken for the skin benefit ingredient to reach the surface of the skin.

The stability of the structured liquid composition and the suspension of the oil or particulate skin benefit ingredient is significantly achieved by the viscosity of the liquid composition produced by the surfactant system present in the lamellar phase. In order to achieve the desired benefits, the liquid cleanser compositions described herein have a viscosity (as measured at 25° C. and a shear rate of 1/sec) of from about 10,000 cps to about 200,000 cps, desirably from about 25,000 cps to about 100,000 cps, and desirably from about 50,000 cps to about 75,000 cps. Although in some embodiments it may be suitable, at a viscosity above about 200,000 cps, the composition begins to become very thick and would generally have poor consumer aesthetics. Within these disclosed viscosity ranges, the structured liquid cleansing product is stable and can suspend the skin benefit ingredient therein such that emulsification is not required to keep the skin benefit ingredient in the solution. As used herein, the term "stable" means that the structured liquid is able to suspend 30 micrometer oil droplets without substantial phase separation at room temperature for a period of at least 3 months.

Suitable surfactants for use in the structured liquid cleanser compositions to achieve the desired cleaning and viscosity properties include anionic surfactants, amphoteric surfactants, zwitterionic surfactants, and combinations thereof. Suitable anionic surfactants include, for example, alkyl sulfates, alkyl ether sulfates, alkali metal or ammonia salts of alkyl sulfates, alkali metal or ammonia salts of alkyl ether sulfates, alkyl phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, and combinations thereof.

Suitable amphoteric surfactants include, for example, betaines, alkylamido betaines, sulfobetaines, N-alkyl betaines, sultaines, amphoacetates, diamphoacetates, imidazoline carboxylates, sarcosinates, acylamphoglycinates, such as cocamphocarboxyglycinates and acylamphopropionates, and combinations thereof.

Suitable zwitterionic surfactants include, for example, 4-[N,N-di(2-hydroxyethyl)-N-octadecylammonio]-butane-1-carboxylate, 5-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

In one embodiment of the present invention, along with the surfactant system and the water, the structured liquid cleanser composition comprises a lipid phase in an amount of from about 1% (by weight) to about 30% (by weight). The lipid phase comprises from about 1% (by weight) to about 5% (by weight) of a sterol or sterol derivative and from about 95% (by weight) to about 99% (by weight) of a natural fat or oil. When applied to the skin, the lipid phase of the structured liquid cleanser composition may act as a skin barrier enhancing agent; that is, one or more components of the lipid phase may penetrate through the surface of the skin and into the viable layers of the skin and replace or add various components, such as lipids, to the skin to improve skin health. For example, lipids may penetrate into the skin and correct a defective epidermal barrier in the skin and may further fortify the barrier to prevent its disruption due to environmental insults. Further, some components may also provide a moisturization benefit to one or more layers of the skin, resulting in increased skin hydration and health.

Suitable sterols or sterol derivatives for inclusion in the lipid phase of the liquid cleanser composition include beta sterols having a tail on the 17 position and having no polar groups, cholesterol, sitosterol, stigmasterol, ergosterol, $C_{10}$-$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyidecanoate, dihydrolanosterol, dihydrolanosteryl octyldecanoate, ergocalciferol, tall oil sterol, soy sterol acetate, lanasterol, soy sterol, avocado sterols, sterol esters, and mixtures thereof.

The term "natural fat or oil" is intended to include fats, oils, essential oils, essential fatty acids, non-essential fatty acids, phospholipids, and mixtures thereof. Suitable fats and oils include Apricot Kernel Oil, Avocado Oil, Babassu Oil, Borage Seed Oil, Butter, $C_{12}$-$C_{18}$ Acid Triglyceride, Camellia Oil, Canola Oil, Caprylic/Capric/Lauric Triglyceride, Caprylic/Capric/Linoleic Triglyceride, Caprylic/Capric/Stearic Triglyceride, Caprylic/Capric Triglyceride, Carrot Oil, Cashew Nut Oil, Castor Oil, Cherry Pit Oil, Chia Oil, Cocoa Butter, Coconut Oil, Cod Liver Oil, Corn Germ Oil, Corn Oil, Cottonseed Oil, $C_{10}$-$C_{18}$ Triglycerides, Egg Oil, Epoxidized Soybean Oil, Evening Primrose Oil, Glyceryl Triacetyl Hydroxystearate, Glyceryl Triacetyl Ricinoleate, Glycosphingolipids, Grape Seed Oil, Hazelnut Oil, Human Placental Lipids, Hybrid Safflower Oil, Hybrid Sunflower Seed Oil, Hydrogenated Castor Oil, Hydrogenated Castor Oil Laurate, Hydrogenated Coconut Oil, Hydrogenated Cottonseed Oil, Hydrogenated $C_{12}$-$C_{18}$ Triglycerides, Hydrogenated Fish Oil, Hydrogenated Lard, Hydrogenated Menhaden Oil, Hydrogenated Mink Oil, Hydrogenated Orange Roughy Oil, Hydrogenated Palm Kernel Oil, Hydrogenated Palm Oil, Hydrogenated Peanut Oil, Hydrogenated Shark Liver Oil, Hydrogenated Soybean Oil, Hydrogenated Tallow, Hydrogenated Vegetable Oil, Lanolin and Lanolin Derivatives, Lard, Lauric/Palmitic/Oleic Triglyceride, *Lesquerella* Oil, Linseed Oil, *Macadamia* Nut Oil, Maleated Soybean Oil, Meadowfoam Seed Oil, Menhaden Oil, Mink Oil, Moringa Oil, *Mortierella* Oil, Neatsfoot Oil, Oleic/Linoleic Triglyceride, Oleic/Palmitic/Lauric/Myristic/Linoleic Triglyceride, Oleostearine, Olive Husk Oil, Olive Oil, Omental Lipids, Orange Roughy Oil, Palm Kernel Oil, Palm Oil, Peach Kernel Oil, Peanut Oil, Pengawar Djambi Oil, Pentadesma Butter, Phospholipids, Pistachio Nut Oil, Placental Lipids, Rapeseed Oil, Rice Bran Oil, Safflower Oil, Sesame Oil, Shark Liver Oil, Shea Butter, Soybean Oil, Sphingolipids, Sunflower Seed Oil, Sweet Almond Oil, Tall Oil, Tallow, Tribehenin, Tricaprin, Tricaprylin, Triheptanoin, Trihydroxymethoxystearin, Trihydroxystearin, Triisononanoin, Triisostearin, Trilaurin, Trilinolein, Trilinolenin, Trimyristin, Trioctanoin, Triolein, Tripalmitin, Trisebacin, Tristearin, Triundecanoin, Vegetable Oil, Walnut Oil, Wheat Bran Lipids, Wheat Germ Oil, Zadoary Oil, oil extracts of various other botanicals, and the like, as well as mixtures thereof.

Suitable fatty acids include Arachidic Acid, Arachidonic Acid, Behenic Acid, Capric Acid, Caproic Acid, Caprylic Acid, Coconut Acid, Corn Acid, Cottonseed Acid, Hydrogenated Coconut Acid, Hydrogenated Menhaden Acid, Hydrogenated Tallow Acid, Hydroxystearic Acid, Isostearic Acid, Lauric Acid, Linoleic Acid, Linolenic Acid, Linseed Acid, Myristic Acid, Oleic Acid, Palmitic Acid, Palm Kernel Acid, Pelargonic Acid, Ricinoleic Acid, Soy Acid, Stearic Acid, Tall Oil Acid, Tallow Acid, Undecanoic Acid, Undecylenic Acid, Wheat Germ Acid, and the like, as well as mixtures thereof.

Suitable essential oils include Anise Oil, Balm Mint Oil, Basil Oil, Bee Balm Oil, Bergamot Oil, Birch Oil, Bitter Almond Oil, Bitter Orange Oil, *Calendula* Oil, California Nutmeg Oil, Caraway Oil, Cardamom Oil, Chamomile Oil, Cinnamon Oil, Clary Oil, Cloveleaf Oil, Clove Oil, Coriander Oil, Cypress Oil, Eucalyptus Oil, Fennel Oil, Gardenia Oil, Geranium Oil, Ginger Oil, Grapefruit Oil, Hops Oil, Hyptis Oil, Indigo Bush Oil, Jasmine Oil, Juniper Oil, Kiwi Oil, Laurel Oil, Lavender Oil, Lemongrass Oil, Lemon Oil, Linden Oil, Lovage Oil, Mandarin Orange Oil, Matricaria Oil, Musk Rose Oil, Nutmeg Oil, Olibanum, Orange Flower Oil, Orange Oil, Patchouli Oil, Pennyroyal Oil, Peppermint Oil, Pine Oil, Pine Tar Oil, Rose Hips Oil, Rosemary Oil, Rose Oil, Rue Oil, Sage Oil, *Sambucus* Oil, Sandalwood Oil, Sassafras Oil, Silver Fir Oil, Spearmint Oil, Sweet Marjoram Oil, Sweet Violet Oil, Tar Oil, Tea Tree Oil, Thyme Oil, Wild Mint Oil, Yarrow Oil, Ylang Ylang Oil, and the like, as well as mixtures thereof.

Some preferred natural fats and oils include, but are not limited to Avocado Oil, Apricot Oil, Babassu Oil, Borage Oil, Camellia oil, Canola oil, Castor Oil, Coconut oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Phospholipids, Rapeseed Oil, Palmitic Acid, Stearic Acid, Linoleic Acid, Rose Hip Oil, Sunflower Oil, Soybean Oil, PROLIPID 141 (proprietary blend of Glyceryl Stearate, Fatty Acids, Lecithin, and Phospholipids from International Specialty Products, Wayne, N.J.) and the like, as well as mixtures thereof.

In another embodiment of the present invention, the lipid phase described above additionally comprises from about 0.5% (by weight) to about 2% (by weight) of a ceramide or ceramide derivative. Because ceramides comprise about 40% of epidermal lipids, they are a major skin component that are important because of their large weight contribution and structural characteristics. Ceramides provide a moisturization benefit to the skin by increasing water retention therein and are necessary for normal skin cell desquamation. Although many ceramides or ceramide derivatives are suitable for inclusion in the lipid phase described above, some preferred ceramides or ceramide derivatives include glucosylceramides, acylceramide, bovine ceramides, sphingolipid E, and combinations thereof.

To ensure that one or more components of the lipid phase remains on the skin after washing with the liquid cleanser composition described herein and rinsing, in one embodiment the lipid phase comprises suspended small droplets of the components. These small droplets are generally more likely to remain on the skin after washing as compared to larger droplets that are easily rinsed off during washing. Generally, it is preferred that the droplets forming the lipid phase of the liquid cleanser composition have a size less than about 30 micrometers, desirably less than about 20 micrometers, and still more desirably less than about 10 micrometers. At these sizes, the droplets are substantially likely to remain on the skin after the washing is complete and can impart the desired benefit.

In order to ensure that the droplets that comprise the lipid phase of the liquid cleanser composition have a suitable size for application to the skin, in some embodiments it may be beneficial to introduce into the lipid phase of the structured liquid composition from about 0.1% (by weight of the lipid phase) to about 4% (by weight of the lipid phase) of a surfactant or a combination of surfactants having an HLB of from about 4 to about 8. Suitable surfactants include sorbitan monooleate, sorbitan stearate, sorbitan monolaurate, polyoxyethylene sorbitan beeswax, polyoxyetheylene 2 cetyl ether, polyoxyethylene 2 stearyl ether, polyoxyethylene 2 oleyl ether, and the like. The surfactant helps reduce the droplet size of the lipid phase by reducing interfacial tension between the oil droplet and the water. A small amount of a surfactant with an HLB of from about 4 to about 8 is preferred to prevent the emulsification of the lipid phase into the water contained in the formulation. These surfactants having an HLB of from about 4 to about 8 do not substantially affect the lamellar structured composition as the surfactants having an HLB of from about 4 to about 8 are mixed with the oil or particulate and surround the oil or particulate.

In addition to the water, surfactant, and lipid phase, the liquid cleanser composition may also optionally comprise one or more optional ingredients to impart additional benefits to the composition. Some optional ingredients may include, for example, antimicrobial actives, antifungal actives, antiseptic actives, antioxidants, astringents, anti-dandruff actives, biological actives, colorants, deodorants, emollients, film formers, fragrances, lubricants, humectants, natural moisturizing agents, preservatives, skin conditioning agents, skin exfoliating agents, skin protectants, solvents, solubilizing agents, suspending agents, wetting agents, and combinations thereof.

In another embodiment of the present invention, a skin protectant can be combined with the water and surfactant components described above to produce a structured liquid cleanser composition comprising a suspended skin protectant. Skin protectants are beneficial skin compounds that gather on the skin's surface to provide a physical barrier on the surface to keep penetrants from penetrating through the skin's surface and into the skin. Additionally, some skin protectants may reduce the loss of moisture from the skin resulting in increased skin hydration. Generally, the skin protectant will be present in the liquid cleanser composition in an amount of from about 1% (by weight) to about 30% (by weight).

Suitable skin protectants for inclusion in the liquid cleanser compositions include, for example, polydimethylsiloxanes such as dimethicone, dimethicone gum, cyclomethicones, and combinations thereof, organo-functional polydimethylsiloxanes including alkyl, amine, and polyether-functional polydimethylsiloxanes, silicone gums, silicone elastomers, silicone resins, silicone polyamides, petrolatum, lanolin, acrylates/dimethicone methacrylate copolymers, allantoin, calamine, cod liver oil, escin, oil soluble botanical extracts, kaolin, laponite, zinc oxide, mineral oil, shark liver oil, talc, zinc acetate, zinc carbonate, and mixtures thereof.

Similar to the lipid phase described above, to ensure that the skin protectant component of the liquid cleanser composition remain on the skin after washing, in one embodiment the skin protectant is comprised of small droplets and/or particulates. These small droplets and/or particulates are generally more likely to remain on the skin after washing as compared to larger droplets that are easily rinsed off during washing. Generally, it is preferred that the droplets and/or particulates of skin protectant component of the liquid cleanser composition have a size less than about 30 micrometers, desirably less than about 20 micrometers, and still more desirably less than about 10 micrometers. At these sizes, the droplets and/or particulates are substantially likely to remain on the skin after the washing is complete and can impart the desired benefit. The size of these droplets may also be controlled by adding a low HLB surfactant as described above.

In addition to the water, surfactant, and skin protectant, the liquid cleanser composition may also optionally comprise one or more optional ingredients to impart additional benefits to the composition. Some optional ingredients may include, for example, antimicrobial actives, antifungal actives, antiseptic actives, antioxidants, astringents, anti-dandruff agents, biological actives, colorants, deodorants, emollients, film formers, fragrances, lubricants, humectants, preservatives, natural moisturizing agents, skin conditioning agents, skin exfoliating agents, skin protectants, solvents, solubilizing agents, suspending agents, wetting agents, and combinations thereof.

In another embodiment of the present invention, a sunscreen active can be combined with the water and surfactant components described above to produce a structured liquid cleanser composition comprising a suspended sunscreen active. Sunscreen actives are beneficial when applied to the skin as they reduce the likelihood of sunburn and the corresponding damage to the skin. Generally, the sunscreen active will be present in the liquid cleanser composition in an amount of from about 1% (by weight) to about 30% (by weight).

Suitable sunscreen actives include benzophenone-8, butyl methoxydibenzoymethane, cinoxate, DEA-methoxycinnamate, digalloyl trioleate, 1-(3,4-dimethoxyphenyl)-4,4-dimethyl-1,3-pentanediene, ethyl dihydroxypropyl PABA, ethylhexyl dimethyl PABA, ethylhexyl methoxycinnamate, ethylhexyl salicylate, 4-(2-Beta-Blucopyranosiloxy) propoxy-2-hydroxybenzophenone, glyceryl PABA, homosalate, mentyl anthranilate, octocrylene, PABA, phenylbenzimidazole sulfonic acid, red petrolatum, TEA salicylate, titanium dioxide, zinc oxide, surface treated titanium dioxide, surface treated zinc oxide, *Spirulina Platensis* Powder, *Vitis Vinifera* seed extract, *Helianthus Annus* seed extract, tocopherol, terephthalidene dicamphor sulfonic acid, drometrizole trisiloxane, benzylylidene malonate polysiloxane, diethylhexylbutamido triazone, methylene-bis-benzotriazolyl tetramethylbutylphenol, disodium phenyl dibenzimidazole tetrasulfonate, bis-ethylhexyloxyphenol methoxyphenyl triazine, diethylamino hydroxybenzoyl hexyl benzoate, and combinations thereof.

In addition to the water, surfactant, and sunscreen active, the liquid cleanser composition may also optionally comprise one or more optional ingredients to impart additional benefits to the composition. Some optional ingredients may include, for example, humectants, preservatives, antimicrobial actives, antifungal actives, antiseptic actives, antioxidants, astringents, biological actives, colorants, deodorants, emollients, film formers, fragrances, lubricants, natural moisturizing agents, skin conditioning agents, skin exfoliating agents, skin protectants, solvents, solubilizing agents, suspending agents, wetting agents, and combinations thereof.

Similar to the lipid phase and skin protectants described above, to ensure that the sunscreen active component of the liquid cleanser composition remains on the skin after washing, in one embodiment the sunscreen active is comprised of small droplets and/or particulates. These small droplets and/or particulates are generally more likely to remain on the skin after washing as compared to larger droplets that are easily rinsed off during washing. Generally, it is preferred that the droplets of sunscreen active component of the liquid cleanser composition have a size less than about 30 micrometers, desirably less than about 20 micrometers, and still more desirably less than about 10 micrometers. At these sizes, the droplets are substantially likely to remain on the skin after the washing is complete and can impart the desired benefit. The size of these droplets may be controlled by adding a low HLB surfactant as described above.

In another embodiment of the present invention, a lipid, skin protectant, or sunscreen active can be microencapsulated and combined with water and the surfactant components described herein to produce a structured liquid cleanser composition comprising a suspended microencapsulated or polymeric entrapped material containing the lipid, skin protectant, and/or sunscreen active. Generally, the microencapsulated or polymeric entrapped particle comprising the lipid, skin protectant, and/or sunscreen active will be present in the liquid cleanser composition in an amount of from about 1% (by weight) to about 30% (by weight).

Similar to the other embodiments described herein, to ensure that the microencapsulated material or polymeric entrapped material of the liquid cleanser composition remains on the skin after washing, the microencapsulated or polymeric entrapped material comprises small particulates. These small particulates are generally more likely to remain on the skin after washing as compared to larger droplets or particulates that are easily rinsed off during washing. Generally, it is preferred that the particulates have a size less than about 30 micrometers, desirably less than about 20 micrometers, and still more desirably less than about 15 micrometers. At these sizes, the particulates are substantially likely to remain on the skin after washing is complete and can impart the desired benefit. As noted above, the size of the particulates or droplets may be controlled by adding a surfactant having an HLB of from about 4 to about 8.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A liquid cleanser composition comprising a lamellar structured liquid comprising from about 30% (by weight) to about 80% (by weight) of a surfactant, from about 1% (by weight) to about 30% (by weight) of a lipid phase, and from about 19% (by weight) to about 69% (by weight) water, wherein the lipid phase comprises from about 1% (by weight) to about 5% (by weight) of a sterol and from about 95% (by weight) to about 99% (by weight) of a natural fat or oil, and wherein the liquid cleanser composition has a viscosity of from about 10,000 cps to about 200,000 cps, and wherein the components of the lipid phase are microencapsulated.

2. The liquid cleanser composition as set forth in claim 1 wherein the lipid phase additionally comprises from about 0.5% (by weight) to about 2% (by weight) of a ceramide or ceramide derivative.

3. The liquid cleanser composition as set forth in claim 1 wherein the liquid cleanser composition has a viscosity of from about 25,000 cps to about 100,000 cps.

4. The liquid cleanser composition as set forth in claim 1 wherein the liquid cleanser composition has a viscosity of from about 50,000 cps to about 75,000 cps.

5. The liquid cleanser composition as set forth in claim 1 wherein the surfactant is selected from the group consisting of anionic surfactants, amphoteric surfactants, zwitterionic surfactants, and combinations thereof.

6. The liquid cleanser composition as set forth in claim 5 wherein the anionic surfactants are selected from the group consisting of alkyl sulfates, alkyl ether sulfates, alkali metal or ammonia salts of alkyl sulfates, alkali metal or ammonia salts of alkyl ether sulfates, alkyl phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, and combinations thereof.

7. The liquid cleanser composition as set forth in claim 5 wherein the amphoteric surfactants are selected from the group consisting of betaines, alkylamido betaines, sulfobetaines, N-alkyl betaines, sultaines, amphoacetates, diamphoacetates, imidazoline carboxylates, sarcosinates, acylamphoglycinates, and combinations thereof.

8. The liquid cleanser composition as set forth in claim 7 wherein the acylamphoglycinates are selected from the group consisting of cocamphocarboxyglycinates and acylamphopropionates.

9. The liquid cleanser composition as set forth in claim 5 wherein the zwitterionic surfactants are selected from the group consisting of 4-[N,N-di(2-hydroxyethyl)-N-octadecylammonio]-butane-1-carboxylate, 5-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonia)-2-hydroxypropane-1-sulfonate, 4-[N,N-di(2-hydroxyethyl)-N-(2-hydroxydodecyl)ammonia]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

10. The liquid cleanser composition as set forth in claim 1 wherein the natural fat or oil is selected from the group consisting of Avocado Oil, Apricot Oil, Babassu Oil, Borage Oil, Camellia oil, Canola oil, Castor Oil, Coconut oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Phospholipids, Rapeseed Oil, Palmitic Acid, Stearic Acid, Linoleic Acid, Rose Hip Oil, Sunflower Oil, Soybean Oil, Lethicin, PROLIPID 141, and mixtures thereof.

11. The liquid cleanser composition as set forth in claim 1 wherein the sterol is a beta sterol having a tail on the 17 position and having no polar groups.

12. The liquid cleanser composition as set forth in claim 1 wherein the sterol is selected from the group consisting of cholesterol, sitosterol, stigmasterol, ergosterol, $C_{10}$-$C_{30}$ cholesterol/lanosterol, cholecalciferol, cholesteryl hydroxystearate, cholesteryl isostearate, cholesteryl stearate, 7-dehydrocholesterol, dihydrocholesterol, dihydrocholesteryl octyidecanoate, dihydrolanosterol, dihydrolanosteryl octyldecanoate, ergocalciferol, tall oil sterol, soy sterol acetate, lanasterol, soy sterol, avocado sterols, sterol esters, and mixtures thereof.

13. The liquid cleanser composition as set forth in claim 2 wherein the ceramide or ceramide derivative is selected from the group consisting of glucosylceramides, acylceramide, bovine ceramides, sphingolipid E, and combinations thereof.

14. The liquid cleanser composition as set forth in claim 1 further comprising an optional ingredient selected from the group consisting of humectants, preservatives, antimicrobial actives, antifungal actives, antiseptic actives, antioxidants, astringents, anti-dandruff agents, biological actives, colorants, deodorants, emollients, film formers, fragrances, lubricants, natural moisturizing agents, skin conditioning agents, skin exfoliating agents, skin protectants, solvents, solubilizing agents, suspending agents, wetting agents, and combinations thereof.

15. The liquid cleanser composition as set forth in claim 1 wherein the lipid phase comprises droplets having a size less than about 30 micrometers.

16. The liquid cleanser composition as set forth in claim 1 wherein the lipid phase comprises droplets having a size less than about 20 micrometers.

17. The liquid cleanser composition as set forth in claim 1 wherein the lipid phase comprises droplets having a size less than about 10 micrometers.

18. The liquid cleanser composition as set forth in claim 1 wherein the natural fat or oil is a combination of essential and non-essential fatty acids.

19. The liquid cleanser composition as set forth in claim 1 wherein the lipid phase further comprises from about 0.1% (by weight) to about 4% (by weight) of a surfactant having an HLB of from about 4 to about 8.

20. The liquid cleanser composition as set forth in claim 19 wherein the surfactant having an HLB of from about 4 to about 8 is selected from the group consisting of sorbitan monooleate, sorbitan stearate, sorbitan monolaurate, polyoxyethylene sorbitan beeswax, polyoxyethylene 2 cetyl ether, polyoxyethylene 2 stearyl ether, polyoxyethylene 2 oleyl ether, and combinations thereof.

21. A liquid cleanser composition comprising a lamellar structured liquid comprising from about 30% (by weight) to about 80% (by weight) of a surfactant, from about 1% (by weight) to about 30% (by weight) of a skin protectant, and from about 19% (by weight) to about 69% (by weight) water, and wherein the liquid cleanser composition has a viscosity of from about 10,000 cps to about 200,000 cps, and wherein the skin protectant is microencapsulated.

22. The liquid cleanser composition as set forth in claim 21 wherein the liquid cleanser composition has a viscosity of from about 25,000 cps to about 100,000 cps.

23. The liquid cleanser composition as set forth in claim 21 wherein the liquid cleanser composition has a viscosity of from about 50,000 cps to about 75,000 cps.

24. The liquid cleanser composition as set forth in claim 21 wherein the surfactant is selected from the group consisting of anionic surfactants, amphoteric surfactants, zwitterionic surfactants, and combinations thereof.

25. The liquid cleanser composition as set forth in claim 24 wherein the anionic surfactants are selected from the group consisting of alkyl sulfates, alkyl ether sulfates, alkali metal or ammonia salts of alkyl sulfates, alkali metal or ammonia salts of alkyl ether sulfates, alkyl phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, and combinations thereof.

26. The liquid cleanser composition as set forth in claim 24 wherein the amphoteric surfactants are selected from the group consisting of betaines, alkylamido betaines, sulfobetaines, N-alkyl betaines, sultaines, amphoacetates, diamphoacetates, imidazoline carboxylates, sarcosinates, acylamphoglycinates, and combinations thereof.

27. The liquid cleanser composition as set forth in claim 26 wherein the acylamphoglycinates are selected from the group consisting of cocamphocarboxyglycinates and acylamphopropionates.

28. The liquid cleanser composition as set forth in claim 24 wherein the zwitterionic surfactants are selected from the group consisting of 4-[N,N-di(2-hydroxyethyl)-N-octadecylammonio]-butane-1-carboxylate, 5-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

29. The liquid cleanser composition as set forth in claim 21 wherein the skin protectant is a polydimethylsiloxane.

30. The liquid cleanser composition as set forth in claim 29 wherein the polydimethylsiloxane is selected from the group consisting of dimethicone, dimethicone gum, cyclomethicone, and combinations thereof.

31. The liquid cleanser composition as set forth in claim 21 wherein the skin protectant is an organo-functional polydimethylsiloxane.

32. The liquid cleanser composition as set forth in claim 31 wherein the organo-functional polydimethylsiloxane comprises an organo-functionality selected from the group consisting of alkyl groups, amine groups, and polyether groups.

33. The liquid cleanser composition as set forth in claim 21 wherein the skin protectant is selected from the group consisting of silicone gums, silicone elastomers, silicone resins, silicone polyamides, silicone resins, petrolatum, lanolin, acrylates/dimethicone methacrylate copolymers, allantoin, calamine, cod liver oil, escin, oil soluble botanical extracts, kaolin, laponite, zinc oxide, mineral oil, shark liver oil, talc, zinc acetate, zinc carbonate, and mixtures thereof.

34. The liquid cleanser composition as set forth in claim 21 further comprising an optional ingredient selected from the group consisting of humectants, preservatives, antimicrobial actives, antifungal actives, antiseptic actives, antioxidants, astringents, anti-dandruff agents, biological actives, colorants, deodorants, emollients, film formers, fragrances, lubricants, natural moisturizing agents, skin conditioning agents, skin exfoliating agents, skin protectants, solvents, solubilizing agents, suspending agents, wetting agents, and combinations thereof.

35. The liquid cleanser composition as set forth in claim 21 wherein the skin protectant comprises particulates or droplets having a size less than about 30 micrometers.

36. The liquid cleanser composition as set forth in claim 21 wherein the skin protectant comprises particulates or droplets having a size less than about 20 micrometers.

37. The liquid cleanser composition as set forth in claim 21 wherein the skin protectant comprises particulates or droplets having a size less than about 10 micrometers.

38. The liquid cleanser composition as set forth in claim 21 further comprising from about 0.1% (by weight) to about 4% (by weight) of a surfactant having an HLB of from about 4 to about 8.

39. The liquid cleanser composition as set forth in claim 38 wherein the surfactant having an HLB of from about 4 to about 8 is selected from the group consisting of sorbitan monooleate, sorbitan stearate, sorbitan monolaurate, polyoxyethylene sorbitan beeswax, polyoxyethylene 2 cetyl ether, polyoxyethylene 2 stearyl ether, polyoxyethylene 2 oleyl ether, and combinations thereof.

40. A liquid cleanser composition comprising a lamellar structured liquid comprising from about 30% (by weight) to about 80% (by weight) of a surfactant, from about 1% (by weight) to about 30% (by weight) of a sunscreen active, and from about 19% (by weight) to about 69% (by weight) water, and wherein the liquid cleanser composition has a viscosity of from about 10,000 cps to about 200,000 cps, and wherein the sunscreen active is microencapsulated.

41. The liquid cleanser composition as set forth in claim 40 wherein the liquid cleanser composition has a viscosity of from about 25,000 cps to about 100,000 cps.

42. The liquid cleanser composition as set forth in claim 40 wherein the liquid cleanser composition has a viscosity of from about 50,000 cps to about 75,000 cps.

43. The liquid cleanser composition as set forth in claim 40 wherein the surfactant is selected from the group consisting of anionic surfactants, amphoteric surfactants, zwitterionic surfactants, and combinations thereof.

44. The liquid cleanser composition as set forth in claim 43 wherein the anionic surfactants are selected from the group consisting of alkyl sulfates, alkyl ether sulfates, alkali metal or ammonia salts of alkyl sulfates, alkali metal or ammonia salts of alkyl ether sulfates, alkyl phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, and combinations thereof.

45. The liquid cleanser composition as set forth in claim 43 wherein the amphoteric surfactants are selected from the group consisting of betaines, alkylamido betaines, sulfobetaines, N-alkyl betaines, sultaines, amphoacetates, diamphoacetates, imidazoline carboxylates, sarcosinates, acylamphoglycinates, and combinations thereof.

46. The liquid cleanser composition as set forth in claim 43 wherein the acylamphoglycinates are selected from the group consisting of cocamphocarboxyglycinates and acylamphopropionates.

47. The liquid cleanser composition as set forth in claim 43 wherein the zwitterionic surfactants are selected from the group consisting of 4-[N,N-di(2-hydroxyethyl)-N-octadecylammonio]-butane-1-carboxylate, 5-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio) propane-1-sulfonate, 3-(N,N-dimethyl-N-hexadecylammonia)-2-hydroxypropane-1-sulfonate, 4-[N,N-di(2-hydroxyethyl)-N-(2-hydroxydodecyl)ammonia]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

48. The liquid cleanser composition as set forth in claim 40 wherein the sunscreen active is selected from the group consisting of benzophenone-8, butyl methoxydibenzoymethane, cinoxate, DEA-methoxycinnamate, digalloyl trioleate, 1-(3, 4-dimethoxyphenyl)-4,4-dimethyl-1,3-pentanediene, ethyl dihydroxypropyl PABA, ethylhexyl dimethyl PABA, ethylhexyl methoxycinnamate, ethylhexyl salicylate, 4-(2-Beta-Blucopyranosiloxy)propoxy-2-hydroxybenzophenone, glyceryl PABA, homosalate, mentyl anthranilate, octocrylene, PABA, phenylbenzimidazole sulfonic acid, red petrolatum, TEA salicylate, titanium dioxide, zinc oxide, surface treated titanium dioxide, surface treated zinc oxide, Spirulina Platensis Powder, *Vitis Vinifera* seed extract, *Helianthus* Annus seed extract, tocopherol, terephthalidene dicamphor sulfonic acid, drometrizole trisiloxane, benzylylidene malonate polysiloxane, diethylhexylbutamido triazone, methylene-bis-benzotriazolyl tetramethylbutylphenol, disodium phenyl dibenzimidazole tetrasulfonate, bis-ethylhexyloxyphenol methoxyphenyl triazine, diethylamino hydroxybenzoyl hexyl benzoate, and combinations thereof.

49. The liquid cleanser composition as set forth in claim 40 further comprising an optional ingredient selected from the group consisting of humectants, preservatives, antimicrobial actives, antifungal actives, antiseptic actives, antioxidants, astringents, biological actives, colorants, deodorants, emollients, film formers, fragrances, lubricants, natural moisturizing agents, skin conditioning agents, skin exfoliating agents, skin protectants, solvents, solubilizing agents, suspending agents, wetting agents, and combinations thereof.

50. The liquid cleanser composition as set forth in claim 40 wherein the sunscreen active comprises droplets or particulates having a size less than about 30 micrometers.

51. The liquid cleanser composition as set forth in claim 40 wherein the sunscreen active comprises droplets or particulates having a size less than about 20 micrometers.

52. The liquid cleanser composition as set forth in claim 40 wherein the sunscreen active comprises droplets or particulates having a size less than about 10 micrometers.

53. The liquid cleanser composition as set forth in claim 40 further comprising from about 0.1% (by weight) to about 4% (by weight) of surfactant having an HLB of from about 4 to abut 8.

54. The liquid cleanser composition as set forth in claim 53 wherein the surfactant having an HLB of from about 4 to about 8 is selected from the group consisting of sorbitan monooleate, sorbitan stearate, sorbitan monolaurate, polyoxyethylene sorbitan beeswax, polyoxyethylene 2 cetyl ether, polyoxyethylene 2 stearyl ether, polyoxyethylene 2 oleyl ether, and combinations thereof.

* * * * *

UNITED STATES PATENT AND TRADEMARK OFFICE
CERTIFICATE OF CORRECTION

PATENT NO. : 7,666,824 B2
APPLICATION NO. : 10/829518
DATED : February 23, 2010
INVENTOR(S) : Krzysik et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 763 days.

Signed and Sealed this

Twenty-eighth Day of December, 2010

David J. Kappos
*Director of the United States Patent and Trademark Office*